United States Patent [19]

Diener et al.

[11] 4,415,552

[45] Nov. 15, 1983

[54] COMPOSITION FOR ESTABLISHING IMMUNOLOGICAL TOLERANCE

[75] Inventors: Erwin Diener; Uriel Diner, both of Edmonton, Canada

[73] Assignee: The Governors of The University of Alberta, Edmonton, Canada

[21] Appl. No.: 100,346

[22] Filed: Dec. 5, 1979

Related U.S. Application Data

[63] Continuation-in-part of Ser. No. 9,910, Feb. 6, 1979, abandoned.

[51] Int. Cl.³ .................. A61K 39/35; A61K 39/385; A61K 39/39; A61K 31/72; A61K 31/73; A61K 47/00
[52] U.S. Cl. ........................................ 424/91; 424/88; 424/177; 424/180; 424/271; 424/278; 436/530; 260/112 R; 536/32; 536/43; 536/98
[58] Field of Search .................. 424/8, 12, 85, 88, 91, 424/177, 180, 271, 278; 260/6, 8, 13, 112 A, 112 B; 436/529, 530, 543; 536/32, 43, 98

[56] References Cited

U.S. PATENT DOCUMENTS 3,794,630  2/1974  Mullan .............................. 424/91 X
3,959,080  5/1976  Orth ................................. 424/9 UX

OTHER PUBLICATIONS

Orth et al., Angew. Chem. Internat. Edit., vol. 11, No. 4, 1972, pp. 249–260.
Inman, J. of Immunol., vol. 114, 1975, pp. 704–709.
Howard & Courtenay, Eur J. Immunol., vol. 4, 1974, p. 603.

*Primary Examiner*—Anna P. Fagelson
*Attorney, Agent, or Firm*—Millen & White

[57] ABSTRACT

A water-soluble non-immunogenic carrier, namely carboxymethyl cellulose, is provided which, in attachment to allergens or other haptens, is capable of inducing an immunological tolerance in an individual of a mammalian species to the allergen or hapten. The allergen or hapten is attached to each of a plurality of the carboxyl groups of carboxymethyl cellulose. Tolerance has been induced in mice to three particular haptens, namely 2,4-dinitrophenyl, penicillin G and fluorescein in the specific embodiments of the present invention.

16 Claims, 1 Drawing Figure

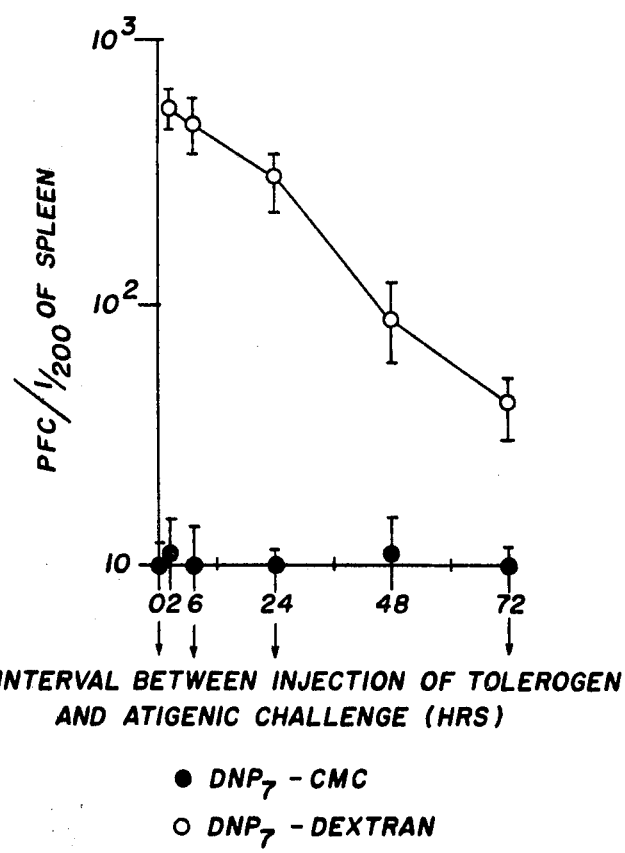

COMPOSITION FOR ESTABLISHING IMMUNOLOGICAL TOLERANCE

CROSS-REFERENCE TO RELATED APPLICATION

This application is a continuation-in-part of my application for U.S. Letters Patent Ser. No. 9,910 filed Feb. 6, 1979, now abandoned.

BACKGROUND OF THE INVENTION

The present invention relates to a composition for inducing immunological tolerance to allergens in an individual of a mammalian species.

Clinicians are faced with an increasingly major problem due to the adverse effects accompanying the administration of certain drugs, particularly antibiotica in their patients. Many pharmaceutical compounds cause an allergic reaction as the patient forms drug specific reagenic antibodies or immunoglobulins, usually of the immunoglobulin class E. In this case immunoglobulin E (IgE) is produced by the body, in response to the presence of the foreign substance or antigen administered, and is specific to combat that antigen. Actually, there are two classes of allergic reaction; one being the humoral antibody production mentioned above wherein cells derived from the bone marrow (B-cells) are responsible for the production of reagenic antibodies of the class IgE. The second component of the immune system is a cell mediated reaction, wherein thymus derived lymphocytes (T-cells) infiltrate the body tissue causing an inflammatory response. In many cases, allergic reactions can be violent or even fatal if they cannot be reversed.

Currently, the most frequently employed solution to the clinical problem of drug allergy is to simply avoid the administration of the drug to which a patient has been found to be allergic.

Research into the field of drug allergy has been directed at inducing a tolerance within the body to certain allergens by administering the allergen in a specific form and dose so as not to trigger an allergic immune response. In particular, it has been found that small molecular sized allergens or haptens can be attached to certain carrier compounds and administered in doses sufficient to induce an immunological tolerance to the allergen.

Previous work done by one of the inventors and described in Transplantation Review 8, 76, 1972, has established the concept that antigens with a repetitive sequence of haptens on a linear molecule acting as a carrier provide the basis for this tolerogenic property.

One of the many problems associated with administering an allergen in attachment to a linear carrier is that the carrier itself, being foreign to the body, triggers an immune response to itself. Thus, a non-immunogenic carrier compound is necessary.

Another property desirable in the carrier is that it be able to disperse the attached allergen throughout the body, so as to induce a total body tolerance thereto. It will be understood that, to be soluble in the body fluids, the carrier in attachment to the allergen must be water soluble.

Thus far, several non-immunogenic or weakly immunogenic carriers have been discovered in this regard, which may serve as vehicles for tolerance induction to clinically relevant drugs, however no system as yet has satisfied all the requirements for a suitable carrier.

Autologous immunoglobulins have been suggested, wherein the hapten is conjugated with the body's own immunoglobulin. This tolerogen however faces the severe potential consequence of triggering an autoimmune reaction, wherein the body begins rejecting self.

Dextran, levan, ficoll and other carbohydrate carriers have been documented as potential tolerogens e.g. see J. G. Howard, B. M. Courtenay, Eur. J. Immunol., 4, 603, 1974. Unfortunately however, these carriers are all immunogenic at appropriate concentrations. This renders them potentially dangerous for clinical use. Thus when administered at concentrations below that for tolerance induction, they not only trigger an immune response to themselves but also to the hapten i.e. allergen attached to them.

It is known in the prior art to use carboxymethyl cellulose as a carrier matrix to immobilize biochemically active compounds, see for example U.S. Pat. No. 3,959,080 issued to Orth et al. For this purpose the carrier molecule must be water insoluble. This is accomplished by chemically cross-linking the polymeric strands of the carboxymethyl cellulose. In a water insoluble form this carrier matrix is not physiologically acceptable to the body.

SUMMARY OF THE INVENTION

The present invention provides a non-immunogenic carrier, namely carboxymethyl cellulose, attached to one or more allergens or other haptens. The novel product is water soluble and is effective in inducing an immunological unresponsiveness to the allergen or other hapten in a mammalian species. The product is inert with respect to the induction of an immune reaction when administered below the dose required to induce unresponsiveness.

Carboxymethyl cellulose (CMC) has been widely used in drug formulations as a stabilizer, and is routinely mixed with antibiotics for human consumption. Studies have been carried out in the past which show CMC to be immunologically inert. Patients hypersensitive to drugs that had routinely been administered to them in the presence of CMC as a dispersing agent, when skin-tested with concentrations of CMC of up to 10 mg/ml, were entirely negative.

This immunological inertness of CMC in man, together with its widespread use in drug formulations singles CMC out from other non-clinically tested compounds which have been suggested as possible tolerogenic carriers for clinical use.

In accordance with three specific embodiments of the present invention, tolerance has been induced to three particular haptens, namely 2,4-dinitrophenyl (DNP), penicillin G (Pen) and fluorescein (F). These haptens were attached to an aminated form of the CMC carrier. Each of the DNP-CMC, Pen-CMC or F-CMC conjungates were injected into groups of mice at a dosage sufficient to induce immunological unresponsiveness to a subsequent challenge with the allergen. After treatment, the mice were shown to have formed the corresponding DNP, Pen or F specific tolerance, as reflected by their inability to respond to a challenge with an immunogenic conjugate of the corresponding hapten.

Broadly stated, the present invention provides a composition for establishing immunological tolerance to an allergen, comprising: a water soluble carboxymethyl cellulose carrier; and a plurality of allergen molecules, each attached to a carboxyl group of the carboxymethyl cellulose.

Preferably the allergen molecules are each attached to an amino group of a water soluble amino alkylated derivative of carboxymethyl cellulose. Most preferably the carboxymethyl cellulose derivative is water soluble N-(2-aminoethyl)carbamylmethylated cellulose.

The invention also broadly contemplates a method of converting an allergen molecule to a form immunologically acceptable for inducing an immunological tolerance in mammals to the allergen. The improvement comprises condensing each of a plurality of allergen molecules to a carboxyl group of a water soluble carboxymethyl cellulose carrier to form a water soluble CMC-allergen conjugate.

Preferably the carboxymethyl cellulose is reacted with a diamine reagent to form a water soluble amino alkylated derivative of carboxymethyl cellulose, and the allergen molecule is condensed to the free amino group. Most preferably the diamine reagent is ethylene diamine used in excess with carboxymethyl cellulose at a pH in the approximate range of 4.7 to 5.3.

The invention also broadly contemplates a method comprising: intravenously or intraperitoneally administering to a patient an effective amoung of water soluble carboxymethyl cellulose having allergen molecules attached thereto, each such allergen molecule being attached to a carboxyl group of the carboxymethyl cellulose, to induce immunological unresponsiveness to a subsequent challenge with the allergen.

DESCRIPTION OF THE DRAWING

FIG. 1 is a graph illustrating the kinetics of tolerance induction with a DNP-CMC conjugate in comparison to a DNP-Dextran conjugate.

DESCRIPTION OF THE PREFERRED EMBODIMENT

In accordance with the embodiments shown herein, carboxymethyl cellulose (CMC) is disclosed in a water soluble form in attachment with 2,4-dinitrophenyl (DNP), Penicillin G (Pen) and fluorescein (F), these being examples of allergens or other haptens which, in conjugation with CMC, are capable of inducing an immunological tolerance (unresponsiveness) specific to that allergen when administered intravenously to a mammalian species. Subsequent injections of the allergen in an immunogenic form, that is in a form which would normally elicit an immune response comprising antibody production specific to combat the allergen, show the animal to have acquired a tolerance to the allergen, and thus to be incapable of producing an immune response to these conjugands.

Although the experimental animals used in the embodiments disclosed were mice, the invention should not be limited thereto. Allergic reactions, in particular those arising from the production of reagenic antibodies of the class IgE, are produced in a wide range of mammalian species which would be patients within the scope of the present invention.

Each of the desired allergen molecules is chemically attached to a carboxyl group of carboxymethyl cellulose (CMC). The method of attaching the allergen to CMC depends on the functionality of the allergen itself. In all cases however, the method of attachment used must ensure that the CMC-allergen conjugate formed is water soluble. Water solubility is essential to ensure that the CMC-allergen conjugate is soluble in the body fluids. To ensure water solubility substantial cross-linking of the CMC polymeric strands must be avoided during the conjugation reaction.

In the embodiments shown herein the allergens DNP, Pen and Fluorescein all exhibit electrophilic centres. For this reason the carboxyl groups of CMC are aminated by reacting CMC with a diamine reagent at appropriate conditions to form a water soluble amino alkylated derivative of CMC. This provides suitable nucleophilic centres on the CMC carrier for attachment to the allergen molecules in an alkaline environment.

Since the diamine is a bifunctional reagent, the above amination reaction must be performed under conditions which prevent any substantial cross linking of the CMC polymeric strands. To that end, one of the amino groups of the diamine should be in an inactive form during the reaction. To accomplish this, one of the amino groups may be reversibly blocked, or more easily, the amination reaction can be performed at acidic conditions which ensure that the monoprotonated species of the diamine is formed. Preferably an excess of the diamine reagent is used to further discourage cross linking.

A water soluble condensing agent may be used to promote the amination reaction. A condensing agent has the general formula $R-N=C=N-R'$, where $R$ and $R'$ are substituents which ensure water solubility.

The most preferred diamine reagent employed is ethylene diamine. At a pH in the range of about 4.7 to 5.3 the predominate species is the monoprotonated form of ethylene diamine. The ethylene diamine is used in excess of the carboxyl groups of the CMC. The pH range may be expanded by increasing the excess of ethylene diamine.

The product formed by reacting CMC with ethylene diamine under the abovedescribed conditions is water soluble N-(2-aminoethyl)carbamylmethylated cellulose. Lyophilization of this compound does not destroy its water solubility, showing that the compound is stable with respect to water solubility.

It will be realized that other methods of attaching an allergen to CMC are within the ability of a skilled chemist. For instance, depending on its functionality, an allergen or a derivative of an allergen may be directly linked to the carboxyl group of CMC provided that the conditions used ensure that a water soluble CMC-allergen conjugate is formed.

By allergen is meant a substance which when introduced into the body by various routes including absoprtion through the skin, inhalation and injection, can cause an adverse reaction by the immune system involving either local or systemic inflammatory responses. These responses may express themselves as eczema, local inflammations and hay fever type reactions, and may in severe cases lead to anaphylactic shock. The latter could be fatal. Exemplary allergens known to be capable of eliciting an allergic reaction include but are not limited to local anasthetics such as novocain, xylocaine and procaine, insecticides, streptomycin, $\beta$-lactam antibiotics, aminoglycoside antibiotics, polypeptide antibiotics, macrolid antibiotics, chloramphenicol, neomycin, sulphonylurea derivatives, sulphonamides, stibophen, rifampicin, quinine, quinidine, pyramidone, phenacetin, isoniazide, insulin, dipyrone, chlorpromazine, antistine, p-aminosalicylic acid, and p-aminobenzoic acid.

Carboxymethyl cellulose is a derivative of cellulose in which some of the hydroxyl groups of the glucose molecules have been synthetically carboxymethylated.

This reaction results in a reduction of the molecular weight of the original cellulose polymer and also in a marked increase in the water solubility. Both the molecular weight and the viscosity of this CMC derivative depend on the number of carboxymethyl groups present in the polymer. It has been found that forms of CMC suitable for the present invention include but are not limited to water soluble CMC characterized by a molecular weight of about 250,000, a degree of polymerization of about 1100, and being approximately 70% carboxymethylated. Forms of CMC having a molecular weight as low as 100,000 were investigated, but showed a low tolerogenic potency. In general it is known that increasing the molecular weight of carbohydrate carries results in both an increase in the tolerogenic potency and the immunological properties. It would be expected that water soluble forms of CMC having a molecular weight greater than 100,000 should be suitable for the present invention.

The following examples are illustrative of the present invention and its effectiveness in inducing an immunological tolerance.

EXAMPLE 1

Preparation of the carboxymethyl cellulose-2,4-dinitrophenyl conjugate (CMC-DNP)

In conjugating carboxymethyl cellulose (CMC) to the desired antigen (hapten), in this case 2,4-dinitrophenyl (DNP), the CMC was first aminated to produce water soluble N-(2-aminoethyl) carbamylmethylated cellulose as described below.

To prepare N-(2-aminoethyl) carbamylmethylated cellulose, 300 mg of the sodium salt of carboxymethyl cellulose (medium viscosity, Sigma C-4888, St. Louis, U.S.A.) were dissolved in 30 ml water. To this was added a solution of 1 ml of ethylenediamine in 4 ml of water whose pH was previously adjusted close to 7 with 6 N HCl, followed by 1 N HCl until the correct pH (7) was obtained. One hundred mg of the condensing agent 1-ethyl-3(3-dimethyl-amino-propyl)-carbodiimide HCl in 2 ml of water were then added, and the pH of this solution adjusted to 5. After 30 minutes the pH of the solution was readjusted to 5. The reaction mixture was left for 2 hours at room temperature and then dialyzed in the cold against water for 2 days. The amino ethyl derivative thus formed was water soluble. Lyophilization did not destroy the water solubility of the product.

Forty-five ml of the amino ethyl derivative thus obtained were used directly for dinitrophenylation as follows. The aminoethyl derivative was reacted with a solution of 20% $Na_2CO_3$ in water to a pH of 9.5 In this solution, 850 mg of 2,4-dinitrobenzene sulfonic acid (DNBS) were added and the pH again adjusted to 9.5. The reaction mixture was left 8 hours at room temperature and then dialyzed against water for 2 days.

The number of DNP groups, or substitution ratio, per 100,000 daltons of CMC was calculated from the absorbency at 360 nm and from the determination of the dry weight of the substance. Dry weight was determined after heating the CMC-DNP conjugate at 75° C. for 48 hours.

Using the above reaction scheme, the substitution ratio varied between 0.24 and 8 DNP groups per 100,000 daltons of CMC. To prepare CMC-DNP conjugates with a smaller substitution ratio, lower amounts of DNBS were used. Hereinafter, the substitution ratio will be indicated by subscripts. Thus $DNP_8CMC$ refers to a substitution ratio of 8 DNP groups per 100,000 daltons CMC.

EXAMPLE 2

Preparation of Carboxymethyl Cellulose-Penicillin Conjugate (CMC-Pen)

N-(2-aminoethyl) carbamylmethylated cellulose was prepared in the manner set forth in Example 1. The amino ethyl derivative was kept at a concentration of 6.5 mg/ml in aqueous solution. Three ml of this solution were diluted to 6 ml with distilled water. The pH was adjusted to 9 with 0.1 N NaOH. One hundred mg of Penicillin G (sodium salt, Sigma Chemicals, St. Louis, U.S.A.) were added at once, and the resulting solution left overnight at room temperature. The solution was then dialyzed in the cold against two daily changes of 2 liters of water for 3 days. The CMC-Pen conjugate thus formed was kept in solution in the cold.

The substitution ratio was determined to be 12 penicillin per 100,000 daltons CMC by dry weight determination, and by the penamaldate assay of Parker (C. W. Parker, Methods in Immunology and Immunochemistry, Vol. 1, page 142, 1967).

EXAMPLE 3

DNP-Specific in vivo Tolerance Induction

The following preparations were needed in demonstrating the effectiveness of the DNP-CMC conjugate of Example 1 in inducing an immunological tolerance.

DNP-Ficoll conjugate—To prepare this DNP-F conjugate, 142 mg of Ficoll (Pharmacia Fine Chemicals, Uppsala, Sweden) were dissolved in 5 ml of water. A solution of 90 mg of CNBr dissolved in 5 ml of water were added at once. The pH of the resulting mixture was adjusted to 10 with 1 N NaOH, and kept at this level for 10 minutes. A solution containing 7 mg of DNP-L-lysine (Sigma Chemicals, St. Louis, U.S.A.) in 3 ml of 1 M $NaCO_3H$ was then added, and the reaction mixture allowed to stand overnight at room temperature. The mixture was dialyzed against phosphate buffered saline at pH 7.2. The substitution ratio as determined by UV absorbance at 360 nm and by dry weight analysis, was 32 DNP groups per 100,000 daltons Ficoll.

Trinitrophenyl-Burro Red Blood Cells conjugate (TNP-BRBC)

A first solution was prepared by suspending 1.5 ml of packed red blood cells in 10 ml of a 0.28 M cacodylate buffer at pH 6.9 in which 120 mg of trinitrobenzene sulphonic acid (Baker, Phillipsburg, N.J., U.S.A.) had been dissolved. After 20 minutes the suspension was poured into 40 ml of a phosphate buffered saline solution containing calcium and magnesium ions at a pH of 7 (PBS Ca Mg). The cells were washed and suspended in 40 ml of the above phosphate buffered saline in which 20 mg of glycylglycine had been dissolved. After 10 minutes in the cold, the cells were washed twice with the abovementioned PBS Ca Mg solution, and finally suspended in 15 ml of the appropriate medium.

Trinitrophenyl-Sheep Red Blood Cells conjugate (TNP-SRBC)

These red blood cells were haptenated in the same manner as used for the BRBC, using only 30 mg of trinitrobenzene sulfonic acid and leaving the first solution for 10 minutes rather than 20 minutes.

In the following example, DNP-Ficoll and TNP-Burro Red Blood Cells were used as immunogenic forms of the hapten DNP to test for the DNP-specific tolerance induction. It should be noted that DNP and TNP are immunologically identical, that is they both elicit antibody which cross-reacts with both haptens. Both molecules were used interchangeably due to the chemical convenience of coupling the haptens to the carriers. DNP-Ficoll is an example of a T-independent antigen, whereas TNP-BRBC is an example of a T-dependent antigen. A T-dependent antigen is one which requires the assistance of a sub-population of thymus derived cells in order to produce an immune response, in contrast to T-independent antigens, which are capable of eliciting an immune response without the co-operation of the T-cells.

Male CBA/CaJ mice of age 60–90 days in groups of five were injected once intravenously with either various concentrations of $DNP_8CMC$, as prepared in Example 1, CMC alone, or saline alone, as set forth in Table 1a. The groups were challenged 24 hours later with either the $DNP_{32}Ficoll$ conjugate, Burro Red Blood Cells (BRBC) or TNP-Burro Red Blood Cells, to test for the specificity and unresponsiveness to DNP. Immunogenic challenge was with either 50 μg $DNP_{32}F$, 0.1 ml of a 10% suspension of BRBC or 0.1 ml of a 10% suspension of TNP-BRBC per mouse.

Five days after this immunogenic challenge, the mice were killed by cervical dislocation and their spleens removed into Michell-Dutton balanced salt solution (MDBSS). The spleen cell suspension was assayed for antibody forming cells according to the assay technique of Cunningham and Szenberg (Cunningham, A., and Szenberg, A., Immunology 14, 599, 1968). In this plaque-forming cell assay (PFC), 1/200 of the spleen in suspension is placed on a lawn of Sheep Red Blood Cells (SRBC) conjugated with TNP. Non-tolerized spleen cells, if present, elicit anti-DNP-specific antibodies of the immunoglobulin classes G and M causing hemolysis of the SRBC, leaving clear plaques in this vicinity, the number of which is theoretically directly proportional to the original number of non-tolerized cells plated. Response to BRBC was assayed in the presence of an enhancing serum. In this regard, trinitrophenylated Burro Red Blood Cells (TNP-BRBC) wee used as targets for IgG with the addition of rabbit anti-mouse IgG antiserum for the development of IgG indirect plaque-forming cells (PFC). Since no IgG response was obtained in the controls challenged with DNP-Ficoll, anti-hapten responses were measured in terms of direct plaques.

The results of the above-described assays are summarized in Table 1(a) and (b). Complete tolerance to the DNP hapten was induced with as little as 250 μg of $DNP_8CMC$ per animal. Tolerance was specific to DNP since no significant difference was observed in the magnitude of the immune response to BRBC between groups of mice injected with $DNP_8CMC$ and those given CMC or saline only. Since no substantial difference was noted in the response to either T-independent or T-dependent antigens, that is to $DNP_{32}F$ or TNP-BRBC respectively, the induced tolerance does not appear to be influenced by sub-populations of T-cells.

TABLE 1

In vivo induction of tolerance to DNP by DNP-CMC

| $DNP_8CMC$ | CMC | Saline | Mean PFC DNP-Ficoll | BRBC |
|---|---|---|---|---|
| (a) Immunogenic challenge with $DNP_{32}Ficoll$ | | | | |
| 700 μg | — | — | 38 ± 19 | 209 ± 94 |
| 250 | — | — | 9 ± 3 | 363 ± 132 |
| 175 | — | — | 74 ± 16 | 330 ± 127 |
| 44 | — | — | 178 ± 59 | 134 ± 38 |
| 11 | — | — | 282 ± 50 | 223 ± 50 |
| — | 250 μg | — | 1039 ± 160 | 389 ± 50 |
| — | — | + | 1022 ± 48 | 263 ± 132 |
| (b) Immunogenic challenge with TNP-BRBC | | | | |
| 250 μg | — | — | 22 ± 4 | 1442 ± 308 |
| — | 250 μg | — | 236 ± 72 | 972 ± 110 |
| (c) Induction of tolerance in hapten primed mice | | | | |
| 250 μg | — | — | 36 ± 13 | 1632 ± 281 |
| — | 250 μg | — | 467 ± 151 | 1520 ± 305 |

To ensure that the state of tolerance to the DNP hapten was apparent not only in the spleen cells, but at the systemic level, the whole blood of the mice was assayed. Hapten specific hemolysine titers were estimated from mice which had been given $DNP_8CMC$ or CMC alone and challenged 24 hours later with $DNP_{32}F$. Seven days following the challenge, the mean ±SD hemolysine titre in a group of 5 mice pretreated with CMC was 28.8±7.1 whereas the hemolysine titre in the group of 5 mice pretreated with $DNP_8CMC$ was less than 1. An hemolysine titre is that dilution of the sera which results in 50% hemolysis of a given amount of haptenated SRBC.

EXAMPLE 4

Passive Cutaneous Anaphylaxis (PCA) Assay for IgE Response

The above methods of assaying for antibody production through PFC are indicative of IgG and IgM responses. In view of the fact that many allergic reactions in man involve the production of IgE antibody, it is also desirable to test CMC as a tolerogenic carrier for an IgE response. An IgE response cannot be directly measured by PFC's as used previously, since IgE does not cause hemolysis, a prerequisite of the PFC assay, but instead causes a local vasodilitation in blood vessels, which is detected by way of the conventional passive cutaneous anaphylaxis (PCA) assay.

Two groups of mice were injected with 250 μg of either Pen-CMC or $DNP_8CMC$. Two control groups were given CMC alone. After 48 hours the groups were immunologically challenged with Keyhole Limpet Hemocyanin (KLH) conjugated to Penicillin G or Avoalbumin (Ova) conjugated to DNP as prepared by the procedures indicated below. After 14 days the animals were bled, and 30 μl of their serum subjected to the PCA assay by injecting it intracutaneously into rats. Four hours later, the rats were given intravenously an immunogenic form of the corresponding allergen, that is, 1 mg of either a bovine gamma gobulin-Pen conjugate or a human gamma gobulin-DNP conjugate, the preparations of which are indicated below, in a 1% Evans blue solution. If the mouse serum that had previously been injected into the rat skin contained any IgE, its vasodilitating property would, upon interaction with the corresponding antigen, lead to the leakage of the Evans's blue dye into the tissue. None of the mice that had received Pen-CMC or DNP-CMC contained any measurable reagenic antibody to Pen or DNP haptens, and were thus tolerized. The mice having received only CMC prior to challenge gave a primary IgE antibody titre to DNP or Pen of between 1/200 and 1/500 which is the dilution of serum injected into the rat skin which will give a positive PCA.

Preparation of the Keyhole Limpet Hemocyanin-Penicillin G conjugate (KLH-Pen)

One hundred mg of KLH (Calbiochem, San Diego, Calif.) were dissolved in 20 ml of water. The pH of the solution was adjusted to 11 with 0.1 N NaOH and 1.5 g of Penicillin G were added at once. The reaction mixture was allowed to stand for 2 hours at room temperature before dialyzing in the cold against two daily changes of 2 liters of water for 3 days. From dry weight determination and penamaldate analysis, the substitution ratio was found to be 52 penicillin molecules per 100,000 daltons KLH.

Preparation of the Bovine Gamma Gobulin-Penicillin G conjugate (BGG-Pen)

The BGG-Pen conjugate was prepared according to the procedure of A. Sehon et al (A. Sehon et al, Journal of Immunology, 117, 927, 1976) as follows:

Five hundred mg of BGG (Sigma Chemicals, St. Louis, U.S.A.) were dissolved in 25 ml of 0.5 M $K_2CO_3$. To this solution 250 mg of Penicillin G were added at once. The reaction mixture, after standing at 37° C. for 24 hours, was dialyzed in the cold against 2 daily changes of 2 liters of water for 2 days. The resulting conjugate was kept in the cold until use.

The rate of substitution as determined by dry weight analysis and the Penamaldate assay was 10 Penicillin molecules per mol of BGG.

Preparation of the Human Gamma Gobulin-Trinitrophenyl conjugate (HGG-TNP)

Three hundred mg of HGG (Sigma Chemicals, St. Louis, U.S.A.) were dissolved in 30 ml of water. To this solution was added a solution of 25 mg/ml of trinitrobenzene sulfonic acid in 10% $Na_2CO_3$. The reaction mixture was allowed to stand for 30 minutes at room temperature. The resulting solution was dialyzed against water until no more yellow color leaked from the dialysis bag. The solution was kept in the cold until use.

The rate of substitution was determined by dry weight analysis and the absorbency at 348 nm at a pH of 7.4. It was found to be 75 molecules TNP per 170,000 daltons HGG.

Preparation of the Avoalbumin-2,4-dinitrophenyl conjugate (Ova-DNP)

This conjugate was prepared according to the method of H. N. Eisen (H. N. Eisen, "Methods in Medical Research", Yearbook Medical Publishers, Vol. 10, pp. 94–102, 1964). The conjugate thus obtained had a substitution ratio of 2 DNP groups per 150,000 daltons avoalbumin as determined from dry weight analysis and the absorbency at 360 nm.

EXAMPLE 5

The Kinetics of Tolerance Induction

To determine whether the unresponsiveness induced by the tolerogen is long lasting, groups of mice were injected with either 250 µg of $DNP_8CMC$ as prepared in Example 1, or with CMC alone. The mice were challenged 21 days later with 50 µg $DNP_{32}F$ as prepared in Example 3 and subjected to the PFC assay.

The control animals yielded a mean $\pm SD$ of $318 \pm 62$ PFC per 1/200 of a spleen, while the mice pretreated with the tolerogen conjugate gave a response of $20 \pm 4$ PFC per 1/200 of a spleen, thus showing the induced tolerance to be effective for at least 21 days.

It may be argued that DNP-CMC, rather than inducing unresponsiveness, merely delays the latent period of the immune response following an immunogenic challenge. This possibility was ruled out by showing that mice pretreated with 250 µg of $DNP_8CMC$ failed to yield an antibody forming cell response when tested 7 days instead of 5 days after an immunogenic challenge. Thus 5 mice pretreated with $DNP_8CMC$ and tested 7 days after an immunogenic challenge with 50 µg $DNP_{32}F$, gave a PFC assay response of $0.6 \pm 1.3$ PFC per 1/200 of a spleen, whereas the control animals pretreated with CMC alone contained $75 \pm 19$ PFC per 1/200 of a spleen. The 7 day control response was lower than the 5 day response, reflecting the normal response kinetics to DNP-F which peaks at 5 days and declines thereafter.

To determine the time interval which is minimally required to induce tolerance with DNP-CMC, 250 µg of $DNP_7CMC$, as prepared in Example 1, were injected into groups of mice. The mice were challenged with 50 µg $DNP_{32}$Ficoll, as prepared in Example 3, at various times after the injection of $DNP_7CMC$.

As evidenced in FIG. 1, unresponsiveness was complete 30 minutes after the administration of $DNP_7CMC$. FIG. 1 additionally illustrates the time interval required to induce tolerance to DNP when mice were challenged after having received 250 µg of another haptenated carbohydrate known to have tolerogenic properties, namely, $DNP_7Dextran$, prepared as by D. Desaymard et al (Desaymard, D., and M. Feldmann, 1975, Eur. J. Immunol. 5,537). $DNP_7$-Dextran effected a gradual decrease in responsiveness over a period of 72 hours.

EXAMPLE 6

Effect of Allergen Substitution Rate

To determine the effect of different hapten substitution rates on the tolerance induction to DNP, DNP-CMC conjugates were prepared, differing in the extent to which they were substituted with the DNP hapten. This was done by varying the amount of 2,4-dinitrobenzene sulfonic acid used in the preparation outlined in Example 1.

Groups of 5 mice were injected with either 250 µg of DNP-CMC conjugates having the hapten substitution ratios listed in Table 2, or with CMC alone. The mice were challenged with 50 µg of $DNP_{32}$Ficoll 24 hours later. The spleens of the mice were removed 4 days later and subjected to the PFC assay described in Example 3.

The results are shown in Table 2. As expected, the tolerogenic property of the conjugate depends on a minimal substitution ratio of DNP. At a concentration of 250 µg of the tolerogen per animal, partial tolerance was achieved with a substitution ratio of 1.2 DNP groups per 100,000 daltons molecular weight of CMC. Tolerance was complete when the substitution ratio was raised to 5 DNP per 100,000 daltons CMC.

TABLE 2

Effect of different hapten substitution rates on in vivo induction of tolerance to DNP by DNP-CMC

| DNP-CMC 250 µg/mouse | CMC 250 µg/mouse | Mean PFC ± SD TNP |
|---|---|---|
| DNP$_{0.24}$CMC | — | 421 ± 103 |
| DNP$_{1.2}$CMC | — | 139 ± 34 |
| DNP$_5$CMC | — | 35 ± 18 |
| — | + | 393 ± 46 |

EXAMPLE 7

Tolerance Induction in Athymic Mammals

It is believed that the tolerogenic properties of the carboxymethyl cellulose conjugates is not in fact due to the activation of subpopulations of suppressor cells in the thymus (T-suppressor cells) which are believed to play a role in activating the undesirable allergic reaction class of cell-mediated immunity.

The following example is included to demonstrate that both normal and athymic mice are equally susceptible to tolerance induction with the DNP-CMC tolerogen. Athymic mice, having no thymus, are deficient in sub-populations of T-suppressor cells.

Groups of 5 athymic Balb/c mice were injected with 250 µg of either DNP$_5$CMC or CMC alone and challenged 24 hours thereafter with 50 µg of DNP$_{32}$Ficoll and a 10% suspension of Burro Red Blood Cells. Five days later the spleens were removed and subjected to a PFC assay as outlined in Example 3.

The results are shown in Table 3, in comparison to the results obtained with groups of normal mice having received the same treatments. The DNP$_5$CMC tolerogen was effective in inducing DNP-specific tolerance in both strains of mice, suggesting that the tolerogen exerts its effect independent of T-suppressor cells.

TABLE 3

Induction of tolerance to DNP by DNP-CMC in normal and athymic Balb/c mice

| | | Mean PFC ± S.D. | |
|---|---|---|---|
| Mice | Treatment | TNP | BRBC |
| normal | CMC | 418 ± 106 | 346 ± 106 |
| normal | DNP$_5$CMC | 53 ± 20 | 518 ± 129 |
| nu/nu | CMC | 243 ± 136 | <1 |
| nu/nu | DNP$_5$CMC | 13 ± 3 | <1 |

EXAMPLE 8

Tolerance Induction After Pre-immunization

In many cases, a clinician finds himself in a situation wherein it is necessary to reverse an allergic reaction. To test then, whether the tolerogen of the present invention would be effective in the case where the animal had already received the allergen in an immunogenic form, groups of 5 mice were given a dose of 50 µg DNP$_{32}$Ficoll 13 days prior to administering 250 µg of DNP$_8$CMC. The mice were challenged with 50 µg of DNP$_{32}$Ficoll and a 10% suspension of BRBC 24 hours later. Five days thereafter, the spleens were subjected to the PFC assay of Example 3. The results of Table 1c show DNP-CMC capable of inducing tolerance in mice that had been pre-immunized with DNP.

EXAMPLE 9

Fluorescein-Specific in vivo Tolerance Induction

Tolerance induction to fluorescein was demonstrated by the method described in Example 3 using the tolerogen carboxymethyl cellulose fluorescein (CMC-F) prepared by the following procedure.

CMC was aminated by the procedure set forth in Example 1 to form water soluble N-(2-aminoethyl) carbamylmethylated cellulose. This amino ethyl derivative was kept at a concentration of 6.5 mg/ml in an aqueous solution. To 45 ml of this solution was added 240 mg of Na$_2$CO$_3$ and the pH adjusted to 9.5 with 2 N HCl. Four mg of fluorescein isothiocyanate (Baltimore Biological Laboratories, Baltimore, U.S.A.) were then added and the pH kept at 9.5 until all the fluorescein had dissolved. The reaction mixture was kept at 4° C. overnight and then dialyzed extensively against water. From dry weight determination and UV absorption at 493 nm using E=60,000, the substitution ratio was determined to be 8 fluorescein molecules per 100,000 daltons CMC. The dose of F$_8$-CMC used in tolerance induction was 250 µg per mouse.

The immunogenic form of fluorescein used to test for tolerance induction was Ficoll-Fluorescein (FF) prepared by the following procedure.

A solution of N-(aminoethyl) carbamylmethylated ficoll, prepared by the method of J. K. Inman, Journal of Immunology, Vol. 114, 704, 1975, was kept at a concentration of 5 mg/ml. To this solution was added 1 mg offluorescein isothiocyanate for every 10 mg of ficoll and the pH adjusted to 9.5 with 0.5 M Na$_2$CO$_3$. Once the fluorescein isothiocyanate had dissolved, the reaction mixture was kept at 4° C. overnight. The mixture was then dialyzed extensively against water. The substitution ratio, as determined by dry weight analysis and UV absorption, was 40 fluorescein molecules per 400,000 daltons ficoll. The dose of F$_{40}$-Ficoll used in the immunogenic challenge was 50 µg per mouse.

In the plaque-forming assay, using 1/400 of the spleen from control and tolerized mice, the mean PFC was 178±41 for the control animal and 8.4±6 for the tolerized animals showing tolerance induction to the fluorescein allergen.

While the present invention has been disclosed to demonstrate carboxymethyl cellulose in attachment with the allergen, 2,4-dinitrophenyl, penicillin G or fluorescein acting as an effective tolerogen, it should be understood that the use of other relevant allergens with carboxymethyl cellulose would be within the skill of those familiar in this art and thus within the spirit and scope of the present invention. The method of attachment, the substitution ratio and the effective dosage would be routine experimental parameters to be established in each case.

The embodiments of the invention in which an exclusive property or privilege is claimed are defined as follows:

1. A pharmaceutically acceptable injectable composition consisting essentially of a water soluble conjugate of:
   a substantially non-cross-linked water soluble carboxymethyl cellulose carrier, and
   a plurality of allergen molecules, each chemically attached to a carboxyl group of the carboxymethyl cellulose carrier, said composition being capable upon injection in a mammal of inducing immunological tolerance to the allergen without evoking an allergenic response to the allergen.

2. A composition as set forth in claim 1 wherein the carrier is a water soluble amino alkylated derivative of carboxymethyl cellulose and the allergen is attached to the amino group thereof.

3. The composition as set forth in claim 2 wherein the allergen is a derivative of the penicillin molecule.

4. The composition as set forth in claim 2 wherein the allergen is 2,4-dinitrophenyl or fluorescein.

5. The composition as set forth in claim 1 which is an aqueous solution.

6. The composition as set forth in claim 2 which is an aqueous solution.

7. A method of converting an allergen molecule to a form immunologically acceptable for inducing an immunological tolerance in mammals to the allergen without evoking an allergenic response thereto, comprising:
condensing each of a plurality of allergen molecules to a carboxyl group of a water soluble carboxymethyl cellulose carrier to form a water soluble carboxymethyl cellulose-allergen conjugate in which the carboxymethyl cellulose strands are substantially non-crosslinked; and recovering the resulting conjugate from the reaction mixture as a pharmaceutically acceptable injectable composition.

8. The method as set forth in claim 7 wherein the carrier is an aminoalkylated derivative of carboxymethyl cellulose having free amino groups and the allergen is attached to said groups.

9. The method as set forth in claim 7, wherein the carrier is produced by:
reacting a water soluble carboxymethyl cellulose with a diamine reagent at conditions such that one of the amino groups is inactive, to form as a carrier for the allergen a water soluble amino alkylated derivative of carboxymethyl cellulose,
activating the previously inactive amino group; and
condensing each of a plurality of allergen molecules to the free amino group to form a water soluble carboxymethyl cellulose-allergen conjugate.

10. A method as set forth in claim 9 comprising:
reacting a water soluble carboxymethyl cellulose with an excess of ethylene diamine at a pH in the approximate range of 4.7 to 5.3 to form water soluble N-(2-aminoethyl)carbamylmethylated cellulose; and
condensing at an alkaline pH, each of a plurality of allergen molecules to the free amino group of the N-(2-aminoethyl)carbamylmethylated cellulose to form a water soluble carboxymethyl cellulose-allergen conjugate.

11. The method as set forth in claim 10 wherein the allergen is a derivative of the penicillin molecule.

12. The method as set forth in claim 10 wherein the allergen is 2,4-dinitrophenyl or fluorescein.

13. The method for inducing immunological tolerance in a patient comprising intravenously or intraperitoneally administering to the patient an amount of a composition of claim 1 effective to induce immunological unresponsiveness to a subsequent challenge with the allergen.

14. A method as set forth in claim 13 wherein the conjugate of the composition administered to the patient is a conjugate of water soluble aminoalkyl derivative of carboxymethyl cellulose and a plurality of allergen molecules, each attached to a free amino group of the carboxymethyl cellulose derivative.

15. The method as set forth in claim 14 wherein the allergen is a derivative of the penicillin molecule.

16. The method as set forth in claim 14 wherein the allergen is 2,4-dinitrophenyl or fluorescein.

* * * * *